(12) United States Patent
Mann et al.

(10) Patent No.: US 8,529,964 B1
(45) Date of Patent: Sep. 10, 2013

(54) METHOD AND COMPOSITION FOR SUPPRESSION AND CONTROL OF CITRUS CANKER AND OTHER PLANT DISEASES

(76) Inventors: Timothy Lee Mann, Sebring, FL (US); Richard A. Tuck, Sebring, FL (US)

( * ) Notice: Subject to any disclaimer, the term of this patent is extended or adjusted under 35 U.S.C. 154(b) by 321 days.

(21) Appl. No.: 12/797,598

(22) Filed: Jun. 9, 2010

Related U.S. Application Data

(60) Provisional application No. 61/333,211, filed on May 10, 2010.

(51) Int. Cl.
*A01N 59/20* (2006.01)
*A61K 33/34* (2006.01)

(52) U.S. Cl.
USPC ........................................................ 424/630

(58) Field of Classification Search
None
See application file for complete search history.

(56) References Cited

U.S. PATENT DOCUMENTS

2007/0191227 A1* 8/2007 Pfeiffer et al. ................ 504/100

OTHER PUBLICATIONS

Hardy, S., Using copper sprays to control diseases in citrus, PrimeFacts 757, Nov. 2007.*
Bridge, L., K-Phite Systemic Fungicide Proved Effective Against Citrus Canker Plan Food Systems, Citrus Canker 2006 Research Report.*
US Environmental Protection Agency Office of Pesticide Programs, Yeast Extract Hydrolysate from *Saccharomyces cerevisiae*, Feb. 2, 2004.*

* cited by examiner

*Primary Examiner* — James H Alstrum Acevedo
*Assistant Examiner* — Thor Nielsen
(74) *Attorney, Agent, or Firm* — Karen Bryant Tripp

(57) ABSTRACT

Method and composition for treating citrus canker on citrus plants. The composition comprises copper nitrate complexed with amino acids from hydrolyzed yeast extract. In the method, an aqueous solution of this composition is sprayed on the plant foliage and absorbed by the plant.

10 Claims, No Drawings

METHOD AND COMPOSITION FOR SUPPRESSION AND CONTROL OF CITRUS CANKER AND OTHER PLANT DISEASES

RELATED APPLICATION

This patent application claims priority from U.S. Provisional Patent Application No. 61/333,211, filed May 10, 2010.

BACKGROUND OF THE INVENTION

1. Field of the Invention

The present invention relates to compositions and methods for treating, suppressing, controlling, and/or preventing citrus canker and other plant diseases inhibited by copper.

2. Description of Relevant Art

The United States Department of Agriculture has reported that citrus canker is a disease caused by the bacterium *Xanthomonas axonopodis* pv. *Citri*, which can cause extensive damage to twigs, leaves, and fruit of susceptible citrus varieties. The disease often causes fruit to drop prematurely and to be unmarketable because of lesions on the peel. The bacteria that cause citrus canker can survive for extensive periods on citrus branches and bark. The disease is spread by wind, rain splash, mechanical activities (such as pruning, picking, and spraying carried out within and between groves), movement of infected plants or plant parts, and the activity of birds, insects, and/or mammals. Citrus canker threatens the citrus growing areas of the United States because of its rapid spread, high potential for damage, and impact on exports to foreign countries and interstate movement.

The University of Florida has reported that over the last 30 years, the Institute of Food and Agricultural Sciences has evaluated dozens of products for canker control, including antibiotics, compounds that reduce resistance in plants, and disinfectants, and none have proven more effective than copper products. Copper products are considered to be quite effective in preventing infection of fruit, less effective for reducing leaf infection, and of limited value in reducing spread of the disease. While applying copper to young leaves generally protects them against infection, such protection is soon lost due to rapid expansion of the surface area as the leaves grow. Fruit grows more slowly and is easier to protect. However, fruit is susceptible to infection after the stomates open, when the fruit is about ½- to 1-inch in diameter, until they develop resistance, and infection through wounds can occur at any stage.

Despite the utility of copper products in treating citrus canker, the University of Florida has advised that copper use should be minimized because copper accumulates in soil and may cause phytotoxicity and environmental concerns. Citrus canker is predicted to be difficult to control. According to the University of Florida, approximately 75% of the citrus acreage in Florida is already within 5 miles of a canker find. An ongoing need exists for improved compositions and methods for treating and controlling citrus canker.

SUMMARY OF THE INVENTION

The composition of the present invention comprises copper, from copper nitrate, complexed with water soluble amino acids or yeast extract that may be absorbed by plants and used by the plants to resist disease. While the invention is effective against any plant disease treatable with or responsive to copper, the invention is especially effective in treating citrus canker on plants in the citrus genus. The amino acids are preferably derived from hydrolyzed Brewer's yeast extract. The method of the invention comprises applying an aqueous solution of the composition of the invention onto the plant, preferably by spraying the solution on the plant foliage.

DETAILED DESCRIPTION OF THE INVENTION

The present invention provides a composition and method for preventing and treating citrus canker in plants, particularly plant species in the citrus genus. The composition and method may also be used for preventing disease in other plants where the disease is known to be reduced or inhibited by copper. The present invention provides a mechanism for introduction of copper into the plant itself, through the plant foliage, to enable the plant to resist disease. This invention thus provides the advantages of copper in treating disease without the disadvantages of copper washing off of the leaves and accumulating in the soil.

That is, most traditional copper pesticides and fungicides are insoluble in water. Such products are typically applied to the plant foliage and provide a characteristic blue coating on the leaves. The copper, while on the leaves, is available to inhibit bacteria that cause citrus canker while on the leaves. However, very little if any of the copper is actually internalized by the plant, and eventually, the copper washes off of the leaves and ends up in the soil.

For the plant to be able to internalize or use the copper, the copper must be in a soluble form that can be taken in by the plants along with water. However, copper metal is known to be insoluble in water and in its pure form cannot be used by plants. Most copper salts are also insoluble in water and thus unusable by plants. Copper chloride is very slightly water soluble and copper fluoride and copper benzoate dehydrate are slightly water soluble. Copper sulfate pentahydrate is soluble in water, with a solubility at 0° C. of 31.6 g per 100 ml. Copper nitrate is very soluble in water, with a solubility at 0° C. of 137.8 g per 100 ml, and thus is the preferred copper salt for use in the present invention. In fact, all of the advantages of the invention can only be realized with copper nitrate as plants are unable to absorb copper sulfate pentahydrate to the degree desired to prevent substantial copper from ending up in the soil, even when the copper sulfate pentahydrate is complexed with amino acids.

According to the present invention, adding amino acids, such as glutamic acid and aspartic acid preferably derived from yeast extract, or preferably adding yeast extract hydrolysate most preferably from *Saccharomyces cerevisiae* or Brewer's yeast (which comprises amino acids), to copper nitrate in an aqueous solution is believed to significantly enhance the uptake of the copper by the plant upon application to the plant foliage. The combination of amino acids or yeast extract with copper nitrate in water results in the copper remaining in solution and enables the plant and plant leaves to internalize the copper. Without wishing to be limited by theory, it is believed that this composition of the present invention provides a water soluble copper complex with the amino acids which effectively neutralizes the positively charged copper so that the negatively charged leaf does not resist its uptake. Rather, when complexed with amino acids, copper is able to move more quickly and easily through the plant cell structure. Further, the copper and amino acid complex of the invention is hygroscopic, attracting moisture from the air to the leaf surface, for availability of the moisture at the leaf surface to facilitate transfer of the complex into the plant. Again without wishing to be limited by theory, it is believed that once in the plant tissue, the copper remains complexed with amino acid for transport in the xylem for use by the plant in resisting disease.

The particular amino acids and the quantity of each in a yeast hydrolysate will vary depending on the particular yeast employed and the growing medium for the yeast. However, all yeasts provide at least the following amino acids: Isoleucine, leucine, lysine, methionine, phenylalanine, threonine, tryptophan, and valine. Yeasts also typically provide arginine, histidine, and cystine, as well as substantial amounts of aspartic acid and glutamic acid.

In a preferred commercial example of the invention, 86 lbs of copper nitrate solution containing 12%-14% copper (Cu) is combined with 14 lbs of commercially available amino acid derived from yeast extract made from hydrolyzed Brewer's yeast and containing 2% nitrogen (1.25% water soluble nitrogen and 0.75% water insoluble nitrogen). This combination results in about 120,000 bioactive units of copper in each gallon. This amount of copper is substantially more than amounts of 22 to 23 bioactive units commonly seen with traditional copper bactericides and fungicides. Moreover, the solution of the invention may be sprayed onto plants and fruit with all types of ground spraying equipment without need to raise the pH of the soil. Raising the pH of the soil has been practiced with traditional copper bactericides and fungicides to immobilize the copper that goes into the soil. However, a raised soil pH can result in less productive plants that are more susceptible to disease. Since virtually all foliarly applied solution of the invention goes into the plant itself, little if any copper goes into the soil to cause adverse effects.

The foregoing description of the invention is intended to be a description of preferred embodiments. Various changes in the details of the described compositions and methods of use can be made without departing from the intended scope of this invention as defined by the appended claims.

What is claimed is:

1. A method of reducing the incidence of citrus canker disease in a plant species comprising applying to the foliage of said plant species a water soluble composition comprising yeast hydrolysate from Brewer's yeast and copper nitrate dissolved in an aqueous solution, such that copper is absorbed into the plant.

2. The method of claim 1 wherein the yeast hydrolysate comprises glutamic acid and aspartic acid.

3. The method of claim 1 wherein essentially no copper is deposited in or remains in the soil.

4. The method of claim 1 wherein the plant species is selected from the genus citrus.

5. The method of claim 1 wherein the composition is applied to the leaves on the plant species.

6. A composition for reducing the incidence of citrus canker disease in a plant species comprising copper nitrate complexed with amino acids and dissolved in an aqueous solution resulting in about 12% to about 14% soluble copper, absorbable by the plant through the plant foliage.

7. The composition of claim 6 wherein the plant species is selected from the genus citrus.

8. The composition of claim 6 wherein the amino acids are derived from yeast hydrolysate.

9. The composition of claim 6 wherein the amino acids comprise arginine, histidine, isoleucine, leucine, lysine, methionine, cystine, phenylalanine, tyrosine, threonine, tryptophan, and valine.

10. The composition of claim 6 wherein the amino acids comprise glutamic acid and aspartic acid.

* * * * *